(12) United States Patent
Maywald et al.

(10) Patent No.: US 6,989,453 B2
(45) Date of Patent: Jan. 24, 2006

(54) METHOD OF PRODUCING A CYCLOHEXENONE OXIME ETHER LITHIUM SALT, PRODUCTS WHICH CAN BE OBTAINED USING THIS METHOD, THE USE THEREOF AND CORRESPONDING PLANT PROTECTION AGENTS

(75) Inventors: Volker Maywald, Ludwigshafen (DE); Reiner Kober, Fussgönheim (DE); Frank Heimann, Ludwigshafen (DE); Klaus Oberdorf, Heidelberg (DE); Albrecht Harreus, Ludwigshafen (DE); Norbert Götz, Worms (DE); Marcus Vossen, Kassel (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 125 days.

(21) Appl. No.: 10/380,107

(22) PCT Filed: Sep. 12, 2001

(86) PCT No.: PCT/EP01/10538

§ 371 (c)(1), (2), (4) Date: Mar. 11, 2003

(87) PCT Pub. No.: WO02/22596

PCT Pub. Date: Mar. 21, 2002

(65) Prior Publication Data

US 2004/0014988 A1  Jan. 22, 2004

(30) Foreign Application Priority Data

Sep. 13, 2000 (DE) ................................. 100 45 131

(51) Int. Cl.
*C07D 335/00* (2006.01)

(52) U.S. Cl. ........................................................ 549/13
(58) Field of Classification Search ............... 504/288; 549/13

See application file for complete search history.

(56) References Cited

U.S. PATENT DOCUMENTS

| | | | | |
|---|---|---|---|---|
| 5,190,573 | A | 3/1993 | Misslitz et al. | 504/292 |
| 6,133,202 | A | 10/2000 | Bratz et al. | 504/244 |
| 6,294,504 | B1 * | 9/2001 | Tobler et al. | 504/246 |
| 6,316,390 | B1 * | 11/2001 | Nakamura et al. | 504/288 |
| 6,383,987 | B1 * | 5/2002 | von der Heyde et al. | 504/271 |
| 6,576,596 | B1 * | 6/2003 | Hill et al. | 504/344 |
| 6,599,861 | B2 * | 7/2003 | Schaetzer et al. | 504/288 |

* cited by examiner

*Primary Examiner*—Deborah C. Lambkin
(74) *Attorney, Agent, or Firm*—Novak Druce & Quigg

(57) ABSTRACT

A process for preparing 2-{1-[2-(4-chlorophenoxy)propoxyimino]-butyl}-3-hydroxy-5-(tetrahydrothiopyran-3-yl)cyclohex-2-enone lithium salt by reacting the corresponding acid 2-{1-[2-(4-chlorophenoxy)-propoxyimino]butyl}-3-hydroxy-5-(tetrahydrothiopyran-3-yl)-cyclohex-2-enone and lithium hydroxide and the isolation of the lithium salt are described. Here, it is advantageous to use a solvent mixture which comprises methanol and at least one aromatic hydrocarbon and to remove at least some of the solvent prior to the isolation. It is particularly preferred to dissolve the acid in an aromatic hydrocarbon, preferably toluene, and to use a methanolic lithium hydroxide solution.

The product, which can be obtained in a more efficient manner by this process, furthermore has considerable advantages with respect to formulation.

18 Claims, No Drawings

METHOD OF PRODUCING A CYCLOHEXENONE OXIME ETHER LITHIUM SALT, PRODUCTS WHICH CAN BE OBTAINED USING THIS METHOD, THE USE THEREOF AND CORRESPONDING PLANT PROTECTION AGENTS

The present invention relates to a process for preparing 2-{1-[2-(4-chlorophenoxy)propoxyimino]butyl}-3-hydroxy-5-(tetrahydrothiopyran-3-yl)cyclohex-2-enone lithium salt from the corresponding acid, to products obtainable by this process, to their use and to crop protection compositions comprising such products.

Cyclohexenone oxime ethers and their metal salts are generally known as useful crop protection agents. They are appreciated in particular as grass herbicides. Metal salts (WO 97/20807) and in particular the cyclohexenone oxime ether lithium salt of the formula (I)

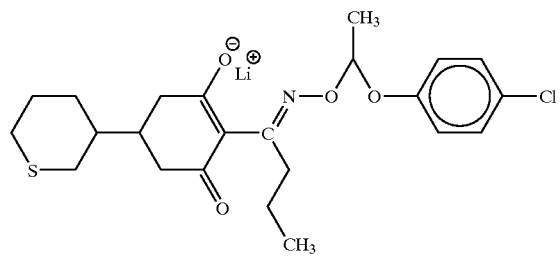

have been found to be particularly suitable.

In addition to the optimization of the properties of the substance, the development of an efficient preparation process is of particular importance with a view to industrial production and use of this active compound.

For the lithium salt described above, WO 97/20807 refers initially to EP 456 112, according to which the corresponding free acid 2-{1-[2-(4-chlorophenoxy)propoxyimino]butyl}-3-hydroxy-5-(tetrahydrothiopyran-3-yl)cyclohex-2-enone is obtained in dissolved form and can then be converted without isolation into the lithium salt.

Similarly to the generally customary procedures for preparing such metal salts by reacting the free acid with a hydride, hydroxide, alkoxide or carbonate of the desired metal ion, WO 97/20807 describes in an exemplary manner the preparation of the Li salt by reaction of a solution of the cyclohexenone oxime ether in toluene with an aqueous lithium hydroxide solution and subsequent removal of the solid fraction formed. Furthermore, in a further example, the lithium salt is prepared by sodium/lithium exchange. Here, in aqueous solution of the corresponding cyclohexenone oxime ether sodium salt is reacted with an aqueous lithium chloride solution and the solid fraction is then separated off.

In the process mentioned first, problems are encountered when separating off the solids fraction formed. Unfavorable filtration properties, in particular high and varying filter resistance, makes isolation of the solid on a pilot-plant and production scale and using customary filtration apparatus such as pressure nutches or centrifuges extremely difficult.

The disadvantage of the process based on sodium/lithium exchange is obvious: initially, the free cyclic hexenone oxime ether has to be converted into the sodium salt in an additional step which is associated with yield loss.

It is an object of the present invention to provide a more efficient process for preparing the cyclohexenone oxime ether lithium salt, in particular with a view to the filtration process, the yield and the purity. We have found that this object is achieved by using a certain solvent mixture as reaction medium.

Accordingly, the present invention provides a process for preparing 2-{1-[2-(4-chlorophenoxy)propoxyimino]butyl}-3-hydroxy-5-(tetrahydrothiopyran-3-yl)cyclohex-2-enone lithium salt of the formula (I),

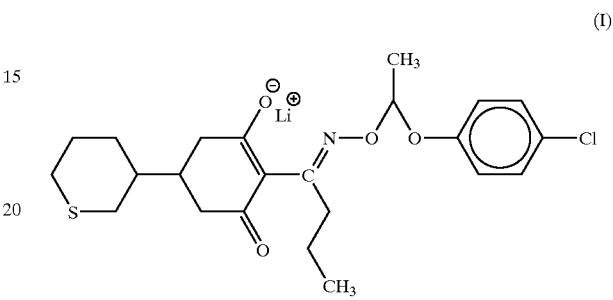

by reacting 2-{1-[2-(4-chlorophenoxy)propoxyimino]butyl}-3-hydroxy-5-(tetrahydrothiopyran-3-yl)cyclohex-2-enone of the formula (II)

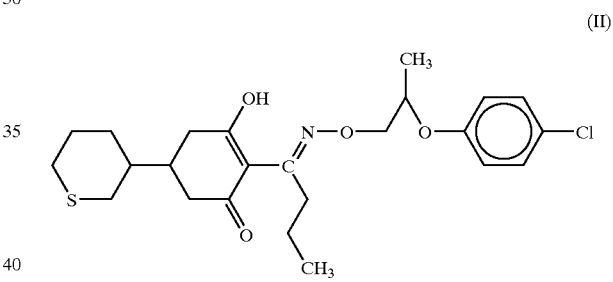

and lithium hydroxide in a solvent mixture and isolating the compound of the formula (I), wherein the solvent mixture comprises at least one aromatic hydrocarbon and methanol and at least some of the solvent is removed prior to the isolation.

Surprisingly, the process according to the invention allows a relatively more efficient isolation of the process product.

The way in which the compounds of the formulae (I), including the formula (I), and (II) are shown includes isomeric forms of these compounds. Particular mention may be made of geometrical and stereoisomers, such as cis/trans isomers, enantiomers or diastereoisomers, and also tautomers, which, in the present case, are based in particular on the enol structure. Accordingly, the compounds of the formula (II), in particular, can also be described as cyclohexane-1,3-dione derivatives. In addition to the substantially pure isomers, the compounds of the formula (I) and (II) also include their isomer mixtures, for example stereoisomer mixtures.

The starting material for the process according to the invention, the cyclohexenone oxime ether 2-{1-[2-(4-chlorophenoxy)-propoxyimino]butyl}-3-hydroxy-5-(tetrahydrothiopyran-3-yl)cyclohex-2-enone of the formula (II)

above can be obtained, for example, by the processes described in WO 97/20807 and EP 456 112. Accordingly, this compound can be obtained in a manner known per se from 2-(1-butyloxy)-3-hydroxy-5-(tetrahydrothiopyran-3-yl)cyclohex-2-enone of the formula (III)

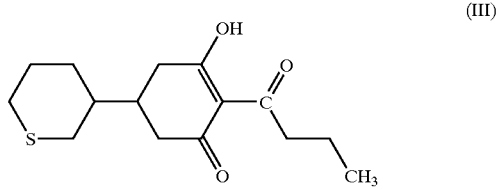

(III)

and the hydroxylamine 1-aminooxy-2-(4-chlorophenoxy)propane of the formula (IV)

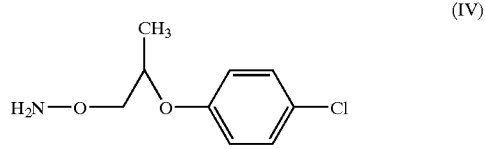

(IV)

One possible way of reacting these compounds is described, for example in EP 169 521. The compounds of the formulae (III) and (IV) can also be employed in the form of their salts, in particular base addition salts of (III) and acid addition salts of (IV). Suitable salt-forming ions are the customary ions, for example metal ions and in particular alkali metal and alkaline earth metal ions, especially sodium, for (III), and halides and in particular sulfates and hydrogen sulfates for (IV). The reaction is preferably carried out in an aqueous reaction medium.

Details about the synthesis of the compound of the formula (III) are given, in particular, in the documents mentioned in EP 456 112. The relevant publications are explicitly included herein in their entirety by way of reference. The compound of the formula (IV) can be synthesized similarly to Houben-Weyl, 10/1 p. 1181 ff.

In its synthesis, the compound of the formula (II) can be isolated after customary work-up of the reaction mixture. However, suitable starting materials for the process according to the invention are also mixtures based on the compound of the formula (II) which are obtained during the synthesis.

Thus, in a particular embodiment of the process according to the invention, the compound of the formula (III) or a salt thereof is reacted with the compound of the formula (IV) or a salt thereof and the reaction product is partitioned in an organic solvent or solvent mixture which preferably contains an aromatic hydrocarbon, in particular the aromatic hydrocarbon to be used according to the invention. To this end, the organic solvent or solvent mixture may be added even during or after the reaction to the preferably aqueous reaction medium. The preferred reaction medium is water or a water-toluene mixture. If required, the pH is adjusted such that the reaction product of the formula (II) is soluble in the organic solvent or solvent mixture. A pH of about 5 to 6 has been found to be expedient.

Thus, the starting material used for the process according to the invention can be a solution of the compound of the formula (II), preferably in an aromatic hydrocarbon and in particular in toluene. This solution can, for example, be the organic phase of the reaction mixture of the above reaction of the compounds (III) and (IV), which, if required, may be concentrated or admixed with more solvent. However, it may also be the organic phase used, after the conversion leading to the compound (II) has ended, for extracting the reaction mixture or the residue obtained following concentration of the reaction mixture, which organic phase can be adjusted to a desired concentration of (II) by concentration or addition of more solvent.

Accordingly, the present invention provides in particular a process for preparing (I) from (III) and (IV) via a solution of (II) without isolating (II) in substance.

According to the invention, the reaction of (II) with lithium hydroxide is carried out in a solvent mixture which comprises methanol and at least one aromatic hydrocarbon.

It is the purpose of the aromatic hydrocarbon or hydrocarbon mixture to dissolve the compound (II). Suitable aromatic hydrocarbons include in particular solvents from the benzene series, such as alkyl-substituted benzenes, for example toluene and xylene. Toluene is especially suitable.

If the compound of the formula (II) is obtained in isolated form, initially at least some of the substance may be dissolved in the aromatic hydrocarbon (mixture) and then be contacted as a solution with the other reactants. If appropriate, it may also be suitable to add substance, i.e., for example, the total amount of (II) or a partial amount thereof, to a reaction mixture which already contains aromatic hydrocarbon. If the compound of the formula (II) is obtained as a solution, it is possible to use this solution if the solvent does not interfere with the reaction according to the invention. It may be necessary to add aromatic hydrocarbon to be used according to the invention to this solution or to the reaction mixture. It may also be useful to remove at least some of the solvent obtained with the solution of compound (II), if appropriate with simultaneous addition of aromatic hydrocarbon.

Preference is given to using a solution of 2-{1-[2-(4-chlorophenoxy)propyloximino]butyl}-5-tetrahydrothiopyran-3-yl-3-hydroxycyclohex-2-en-1-one of the formula (II) which contains at least one aromatic hydrocarbon. Accordingly, at least some of the compound of the formula (II) is dissolved in an aromatic hydrocarbon or an aromatic hydrocarbon mixture. The solution of the compound (II) used is based on at least one aromatic hydrocarbon but may additionally also comprise other solvents. According to a particular embodiment, the solution is a solution of the total amount of compound (II) to be reacted in an aromatic hydrocarbon, preferably toluene.

It may be advantageous to adjust the concentration of the cyclohexenone oxime ether (II) to a desired value. If a solution of the compound (II) is used, the concentration of the compound of the formula (II) is preferably from 5 to 40% by weight, with preference from 10 to 30% by weight and in particular about 20% by weight, based on the total weight of the solution to be used. Thus, a preferred embodiment of the present invention relates to the use of a corresponding toluene solution obtainable, in particular, by adding solvent to a pre-concentrate having a higher concentration of cyclohexenone oxime ether (II).

Lithium hydroxide (LiOH) is generally obtained as a solid. It can be used, for example, in anhydrous form or as hydrate, in particular as monohydrate. Commercially available are, for example, calcined lithium hydroxide or lithium hydroxide monohydrate. These substances are usually available in a chemical purity of at least 98%. For economical reasons, the use of lithium hydroxide monohydrate may be particularly suitable. At least some of the solid can initially be dissolved in methanol, a methanol-containing solvent or another solvent, for example water, and can then be brought into contact as a solution with the other reactants. If appropriate, it may also be possible to add a solid, i.e., for example, the total amount of LiOH or a partial amount thereof as solid to a reaction mixture in which methanol is already present.

Preference is given to reacting a solution of LiOH which contains methanol. Accordingly, at least some of the LiOH is dissolved in methanol or a methanol-containing solvent mixture. What is used is a solution of LiOH which is based on methanol but which may, in addition to methanol, also comprise other solvent. Preference is given to methanolic LiOH solutions which, in addition to possible further solvents, comprise at least 70% by weight, preferably at least 80% by weight and in particular at least 85% by weight of methanol, based on the total amount of solvent in the LiOH solution used. Other possible solvents are, in particular, water and lower alcohols, such as ethanol, propanol and isopropanol. According to a particular embodiment, the solution used is a solution of the total amount of LiOH to be reacted in methanol.

A methanolic LiOH solution advantageously comprises 1 to 7% by weight, preferably 2 to 6% by weight and in particular about 5% by weight of LiOH. The amounts stated are based on the total weight of the solution used, prior to the addition.

The cyclohexenone oxime ether Li salt (I) is obtained by reacting cyclohexenone oxime ether (II) with lithium hydroxide. To this end, the reactants are at least partially dissolved.

As discussed above, it may be advantageous from a technical point of view to initially prepare appropriate solutions and then to bring the solutions into contact with one another, i.e. generally to mix them with each other. However, it is also possible to generate suitable solutions quasi in situ.

Expediently, either the cyclohexenone oxime ether (II) is initially charged, in particular as a solution, and lithium hydroxide is added, in particular as a solution, or conversely lithium hydroxide is initially charged and the cyclohexenone oxime ether (II) is added. It is also possible to add both reactants simultaneously, in particular as solutions, if appropriate to an initial charge of some of the respective solution(s) or of solvent. The addition may take place all at once, a little at a time or continuously. What is obtained is the solvent mixture according to the invention which comprises at least one aromatic hydrocarbon, methanol and, if appropriate, further solvents, for example water. During the course of the reaction, (more) water is formed.

To ensure complete conversion, the lithium hydroxide solution is usually employed in a molar excess. Preference is given to using a molar excess of from 0.5 to 10%, based on the cyclohexenone oxime ether (II) used as starting material. However, it may also be good practice to react lithium hydroxide in a molar ratio of 1:1 with the cyclohexenone oxime ether (II). In this case, for example, the addition of LiOH, in particular as lithium hydroxide solution, may be monitored using a suitable pH electrode and the metered addition may be continued until the equivalents point is reached.

The duration of the metered addition of the reaction partners in question is usually in the range from 10 minutes to 360 minutes, preferably from 10 minutes to 120 minutes, in particular about 30 minutes.

Once all reactants have been added, stirring may be continued until the reaction has gone to completion.

The reaction is usually carried out at temperatures of from −20° C. to 60° C., preferably 0–40° C., particularly preferably 20–30° C.

Prior to the isolation of the cyclohexenone oxime ether salt (I), at least some of the solvent mixture is removed. In particular, methanol is removed from the solvent mixture. This is generally removed together with other components of the solvent mixture, in particular as a methanol/toluene/water mixture.

Removal is preferably carried out by distillation, usually at temperatures between 20 and 70° C., preferably at 30–60° C. and particularly preferably at 40–50° C.

The distillation can be carried out under atmospheric pressure or, preferably, under reduced pressure.

According to a preferred embodiment, the temperature in the reactor is substantially kept constant during the distillation. In this case, it is necessary to vary the pressure when distilling an azeotrope, for example the methanol/toluene/water mixture which is preferred according to the invention. The variation of the pressure is carried out in a manner known per se by the person skilled in the art.

The removal of solvent serves in particular to reduce the amount of dissolved cyclohexenone oxime ether lithium salt (I). The cyclohexenone oxime ether lithium salt (I) precipitates out. It forms a suspension. Accordingly, it may be good practice to remove such an amount of solvent that the compound of the formula (I) precipitates out substantially completely.

According to a particular aspect, the methanol is removed from the reaction mixture substantially completely. Once this has been achieved, the removal of solvent can be stopped. However, it may also be good practice to terminate the removal even earlier. It has been found to be expedient to add fresh methanol to the suspension once the removal of methanol has been terminated. The amount that is to be added should be such that as little as possible and preferably substantially no product redissolves. Typically, from 1 to 100 g, preferably from 5 to 50 g and in particular from 20 to 35 g of methanol may be added per mole of cyclohexenone oxime ether (II).

The cyclohexenone oxime ether lithium salt (I) is usually isolated by subjecting the resulting suspension to a solid/liquid separation. For this purpose, the person skilled in the art has a large number of suitable separation methods at their disposal, in particular sedimentation and filtration steps. Preference is given to filtration, in particular filtration under pressure, belt filtration, vacuum filtration, centrifugation, and the like. In the process according to the invention, the filtration steps can be carried out relatively advantageously since the filter resistances encountered here are relatively low, which allows adequate filtration times to be achieved.

It is generally expedient to purify the solid that has been separated off, in particular in the form of a filter cake. To this end, the solid may be washed with a suitable solvent. Suitable solvents are aromatic hydrocarbons such as benzene, toluene and xylene, aliphatic hydrocarbons, such as pentane, hexane, heptane, petroleum ether, ligroin and cyclohexane, halogenated hydrocarbons, such as dichloromethane, carbon tetrachloride and chlorobenzene, ethers, such as diethyl ether, ethyl-n-propyl ether, di-n-butyl ether, diisopropyl ether, tert-butyl-methyl ether, di-isoamyl ether, cyclohexyl methyl ether, ethylene glycol dimethyl ether, diethylene glycol dimethyl ether, tetrahydrofuran, dioxane, anisol and phenetol, ketones, such as acetone and methyl ethyl ketone, nitriles such as acetonitrile, butyronitrile and benzonitrile, sulfoxides and sulfones, such as dimethylsulfoxide and sulfolane, amides, such as formamide, methylformamide and dimethylformamide, or alcohols, such as methanol, ethanol, propanol, isopropanol, n-butanol, isobutanol, sec-butanol or tert-butanol. It is also possible to use mixtures of these solvents. Particularly suitable is the aromatic hydrocarbon which has already been used for the reaction.

The solvent used for washing can initially be used for rinsing the reaction apparatus, in particular the container, and then be passed through the filter cake, if required a little at a time.

In general, it is also expedient to dry the solid that has been separated off, in particular the filter cake. This may usually be carried out in vacuum drying cabinets, paddle dryers and other devices which serve the same purpose. However, it is also possible to dry the filter cake directly on the filter. This can be carried out, for example, by blow drying using an inert gas such as nitrogen or argon, which may be heated, if required.

The present invention also provides the product which is obtainable by the process according to the invention, i.e. substantially 2-{1-[2-(4-chlorophenoxy)propoxyimino]butyl}-3-hydroxy-5-(tetrahydrothiopyran-3-yl)cyclohex-2-enone lithium salt of the formula (I). The term "substantially" is meant to be understood according to the invention as generally meaning a percentage of at least 90%, preferably at least 95% and in particular at least 98%. In this context, the term describes the content of 2-{1-[2-(4-chlorophenoxy)propoxyimino]butyl}-3-hydroxy-5-(tetrahydrothiopyran-3-yl)cyclohex-2-enone lithium salt of the formula (I) based on the total weight of the product obtainable. A particular form of product obtainable according to the invention has a content of (I) of at least 96% by weight, preferably at least 97% by weight and in particular at least 98% by weight, based on the total weight of the product obtained. Advantageously, the content of organic compounds derived from the compound of the formula (I) and, in the further sense, also from compounds of formulae (II), (III) and/or (IV) is less than 2% by weight and preferably less than 1% by weight.

The present invention also provides crop protection compositions comprising 2-{1-[2-(4-chlorophenoxy)propoxyimino]butyl}-3-hydroxy-5-(tetrahydrothiopyran-3-yl)cyclohex-2-enone lithium salt, preparable by the process according to the invention. Depending on the intended use, the compositions comprise one or more other active compounds, in particular crop protection agents, and/or customary auxiliaries.

The cyclohexenone oxime ether lithium salt (I) or the compositions comprising it can be used, for example, in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, broadcasting or watering. The use forms depend on the intended aims; in each case, they should ensure a very fine distribution of the salt (I) according to the invention.

Suitable inert additives are essentially: mineral oil fractions of medium to high boiling point, such as kerosene and diesel oil, furthermore, coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols, such as methanol, ethanol, propanol, butanol and cyclohexanol, ketones such as cyclohexanone, strongly polar solvents, e.g. amines such as N-methylpyrrolidone and water.

Aqueous use forms can be prepared from emulsion concentrates, suspensions, pastes, wettable powders, water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active substance, wetting agent, tackifier, dispersant or emulsifier and, if appropriate, solvent or oil, which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutylnaphthalene sulfonic acid, and of fatty acids, alkyl- and alkylaryl sulfonates, alkyl sulfates, lauryl ether sulfates and fatty alcohol sulfates, and salts of sulfated hexa-, hepta- and octadecanoles, and also of fatty alcohol glycol ethers, condensates of sulfonated naphthalene and its derivatives with formaldehyde, condensates of naphthalene, of the naphthalene sulfonic acids, with phenol and formaldehyde, polyoxyethylene octyl phenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfide waste liquors or methyl cellulose.

Powders, materials for broadcasting and dusts can be prepared by mixing or grinding the active substances together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The lithium salt and, if appropriate, other active compounds may be present in the compositions in dissolved or undissolved, in particular solid, for example particulate form.

The concentration of the active compound (I) in the ready-to-use preparations may vary within wide ranges, for example from 0.001 to 98% by weight, preferably from 0.01 to 95% by weight. The active compounds are employed in a purity of from 90% to 100%, preferably from 95% to 100% (according to the NMR spectrum).

According to a particular embodiment, the crop protection composition comprises from 1 to 70% by weight of 2-{1-[2-(4-chlorophenoxy)propoxyimino]butyl}-3-hydroxy-5-(tetrahydrothiopyran-3-yl)cyclohex-2-enone lithium salt;

from 0 to 40% by weight of at least one further active compound; and from 0 to 99% by weight of customary auxiliaries.

To widen the spectrum of action and to achieve synergistic effects, the cyclohexenone oxime ether lithium salt (I) may be mixed with a large number of representatives of other herbicidal or growth-regulating active compound groups and applied concomitantly. Suitable components for mixtures are, for example, 1,2,4-thiadiazoles, 1,3,4-thiadiazoles, amides, aminophosphoric acid and its derivatives, amino triazoles, anilides, aryloxy/heteroaryloxyalkanoic acids and their derivatives, benzoic acid and its derivatives, benzothiadiazinones, 2-(hetaroyl/aroyl)-1,3-cyclohexanediones, heteroaryl aryl ketones, benzylisoxazolidinones, meta-$CF_3$-phenyl derivates, carbamates, quinoline carboxylic acid and its derivatives, chloroacetanilides, further cyclohexane-1,3-dione derivates, diazines, dichloropropionic acid and its derivatives, dihydrobenzofurans, dihydrofuran-3-ones, dinitroanilines, dinitrophenols, diphenyl ethers, dipyridyles, halocarboxylic acids and their derivatives, ureas, 3-phenyl uracils, imidazoles, imidazolinones, N-phenyl-3,4,5,6-tetrahydrophthalimides, oxadiazoles, oxiranes, phenols, aryloxy- and heteroaryloxyphenoxypropionic esters, phenyl acetic acid and its derivatives, 2-phenyl propionic acid and its derivatives, pyrazoles, phenylpyrazoles, pyridazines, pyridinecarboxylic acid and its derivatives, pyrimidyl ethers, sulfonamides, sulfonyl ureas, triazines, triazinones, triazolinones, triazolcarboxamides and uracils.

Particularly suitable are N-(butoxymethyl)-2-chloro-N-(2,6-diethylphenyl)acetamide (common name: butachlor), 2-(1,3-benzothiazol-2-yloxy)-N-methyl acetanilide (common name: mefenacet), 3,7-dichloroquinoline-8-carboxylic acid (common name: quinclorac), α-(4,6-dimethoxypyrimidin-2-yl-carbamoylsulfamoyl)-o-toluic acid methyl ester (common name: bensulfuronmethyl), 3-isopropyl-1H-2,1,3-benzothiadiazin-4-(3H)one 2,2-dioxide (common name: bentazone), N-(ethylthiocarbonyl)azepan (common name: molinate), 4-chlorobenzothio N,N-diethylcarbamate (common name: thiobencarb), N-(2-propoxyethyl)-2-chloro-N-(2,6-diethylphenyl)acetamide (common name: pretilachlor), 3,5-bis(methylthiocarbonyl)-2-difluoromethyl-4-(2-methylpropyl)-6-trifluoromethylpyridine (common name: dithiopyr), ethyl 2-[4-(6-chlorobenzoxazol-2-yloxy)phenoxy] propionate (common name: fenoxapropethyl), N-(2-phenylprop-2-yl-thiocarbonyl)piperidine (common name: dimepiperate), 4-(2,4-dichlorobenzoyl)-1,3-dimethylpyrazol-5-yltoluyl-4-sulfonate (common name: pyrazolynate, pyrazolate), 2-[4-(2,4-dichlorobenzoyl)-1,3-dimethylpyrazol-5-yloxy]acetopheno ne (common name: pyrazoxyfen), 2-[4-(2,4-dichloro-m-toluyl)-1,3-dimethylpyrazol-5-yloxy]-4'-meth ylacetophenone (common name: benzofenap), 2-(2-naphthyloxy)propionanilide (common name: naproanilid), methyl 5-(4,6-dimethoxypyrimidin-2-yl-carbamoylsulfamoyl)-1-methylpyrazo 1-4-carboxylate (common name: pyrazosulfuronethyl), 1-(4,6-dimethoxy-1,3,5-triazin-2-yl)-3-[2-(2-methoxyethoxy)phenyl sulfonyl] urea (common name: cinosulfuron), 2-bromo-3,3-dimethyl-N-(1-methyl-1-phenylethyl)butyramide (common name: bromobutide), 1-(1-methyl-1-phenylethyl)-3-p-toluyl urea (common name: dymron, daimuron), $N^2$-(1,2-dimethylpropyl)-$N^4$-ethyl-6-methylthio-1,3,5-triazin-2,4-di amine (common name: dimethametryn), S-benzyl 1,2-dimethylpropyl(ethyl)thiocarbamate (common name: esprocarb), (Z)-N-but-2-enyloxymethyl-2-chloro-2',6'-diethylacetanilide (common name: butenachlor), S-2-methylpiperidinocarbonylmethyl O,O-dipropyl phosphorodithionate (common name: piperophos), (1RS,2SR,4SR)-1,4-epoxy-p-menth-2-yl 2-methylbenzyl ether (common name: cinmethylin), N-(3,4-dichlorophenyl)propanamide (common name: propanil), α-chloro-N-(3-methoxy-2-thienyl)methyl-2',6'-dimethylacetanilide, 4-ethoxybenz-2',3'-dihydrochloranilide, 1-diethylcarbamoyl-3-(2,4,6-trimethylphenylsulfonyl)-1,2,4-triazole, 3-(2-chlorophenylmethyl)-1-(1-methyl-1-phenylethyl) urea, 2-(2-chloro-4-mesylbenzoyl)cyclohexan-1,3-dione, 2,4-dichlorophenoxyacetic acid (common name: 2,4-D), N-(2-chloroimidazole[1,2-a]pyridin-3-yl-sulfonyl)-N' urea (4,6-dimethoxy-2-pyrimidyl) (common name: imazosulfuron), 1-{[2-(cyclopropylcarbonyl)phenyl]aminosulfonyl}-3-(4,6-dimethoxypyrimidin-2-yl) urea, 1-(4,6-dimethoxypyrimidin-2-yl)-3-[1-methyl-4-(2-methyl-2H-tetrazol-5-yl)pyrazol-5-ylsulfonyl] urea, 4-(4-chloro-2-methylphenoxy) butyric acid (common name: MCPB), 2,4-bis(ethylamino)-6-methylthio-1,3,5-triazine (common name: simetryne), 1-[(4,6-dimethoxypyrimidin-2-yl)-3-(2-ethoxyphenoxysulfonyl) urea (common name: ethoxysulfuron).

Further active compounds include, in particular, metal salts of the crop protection agent quinclorac or the aromatic carboxylic acid of the formula (V)

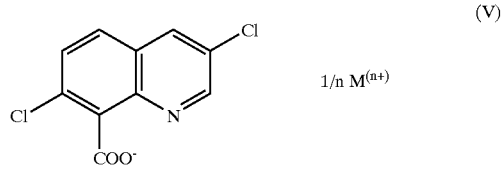

where M is a monovalent (n=1) or divalent (n=2) metal cation.

It may furthermore be advantageous to employ the cyclohexenone oxime ether lithium salt (I), alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The use of 2-{1-[2-(4-chlorophenoxy)propoxyimino]butyl}-5-tetrahydrothiopyran-3-yl-3-hydroxycyclohex-2-en-1-one lithium salt preparable by the process according to the invention as herbicide is also provided by the present invention. This relates to the use as crop protection agent in agriculture, if appropriate in combination with other crop protection agents and/or fertilizers.

Depending on the application method used in each case, the Li salt (I) can be used in a large number of crop plants and ornamental plants for eliminating undesirable plants. Examples of suitable crops are the following:

*Allium cepa, Ananas comosus, Arachis hypogaea, Asparagus officinalis, Beta vulgaris* spp. *altissima, Beta vulagris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Ficus elastica, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum* (*N. rustica*), *Olea europaea, Oryza sativa, Phaseolus lunatus, Phaseolus vulgaris, Picea abies, Pinus* spp., *Pisum sativum, Prunus avium, Prunus persica, Pyrus communis, Ribes sylestre, Ricinus communis, Saccharum officinarum, Secale cereale, Solanum tuberosum,*

Sorghum bicolor (*S. vulgare*), *Theobroma cacao, Trifolium pratense, Triticum aestivum, Triticum durum, Vicia faba, Vitis vinifera, Zea mays.*

The preferred use is the use as rice herbicide.

Furthermore, the cyclohexenone oxime ether lithium salt (I) can also be used in crops which tolerate the action of herbicides.

The salt (I) according to the invention or its preparation can be applied pre- or post-emergence, preferably by foliar treatment. If the active compound is less well tolerated by certain crop plants, application techniques may be used in which the compositions are sprayed, with the aid of the spraying equipment, in such a way that they come into as little contact as possible, if any, with the leaves of the sensitive crop plants, while the active compound reaches the leaves of the undesirable plants growing underneath, or the bare soil surface (post-directed, lay-by).

The rates of application of active compound (I) are from 0.001 to 3.0, preferably from 0.01 to 1.0, kg/ha of active substance (a.s.), depending on the control target, the season, the target plants and the growth stage. Application can be carried out by customary spraying techniques using, for example, water as carrier and amounts of about 100 to 1000 l of spray liquor/ha. Application of the herbicidal compositions by the "low volume" or "ultra-low-volume" process is possible, as is their application in the form of granules.

The cyclohexenone oxime ether Li salt (I) preparable by the process according to the invention surprisingly forms comparatively stable SC formulations, in particular oil SC formulations. This is of importance especially when the salt is used as rice herbicide and, according to a further aspect, for use in tropical regions. Here, it is advantageous if a comparatively high long-term storage stability at an elevated temperature in the range from 30 to 40° C. can be ensured.

The invention is illustrated in more detail by the examples below.

PREPARATION EXAMPLES

Example 1

Product Used: Calcined LiOH (Process A)

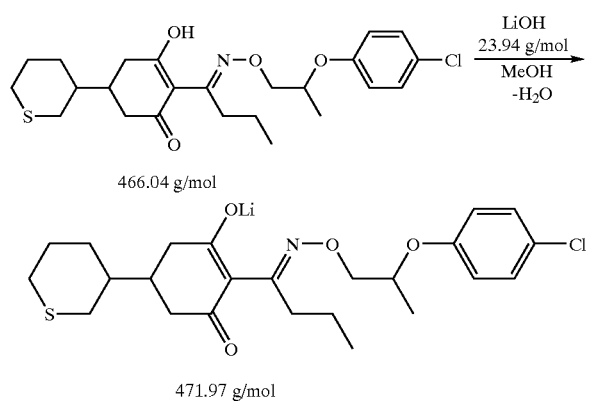

466.04 g/mol 471.97 g/mol

At 25° C., 702.78 g (0.400 mol) of a 26.5% strength solution of the cyclohexenone oxime ether (II) in toluene are initially charged with stirring and diluted with 229.47 g of toluene, thus adjusting the concentration of the cyclohexenone oxime ether (II) to 20%. 200.98 g (0.420 mol) of a 5% strength LiOH solution (calcined LiOH (98+); Chemetall) in MeOH are then introduced over a period of 30 min. The mixture is stirred at 25° C. for 1 h. 370.59 g of a MeOH/toluene/water mixture are then distilled off at 50° C. under reduced pressure. During the distillation, the temperature is kept at 50° C. and the pressure is reduced in a controlled fashion from 450 mbar to 200 mbar. The distillation time is 210 min. Once the distillation has ended, 13 g of methanol are added, the mixture is stirred at room temperature for 15 min and the suspension is discharged from the stirred vessel onto a pressure nutsche. When the filtration has ended, the stirred vessel is rinsed with 174.00 g (200 ml) of fresh toluene and the filter cake is washed with this toluene. The filter cake is then washed twice with in each case 87.0 g (100 ml) of fresh toluene. The filter cake is then dried at 50° C. in a vacuum drying cabinet for 24 h. This gives 181.01 g of filter cake with a content of 98.2%. Taking this content into account, the yield is 94.1%.

Example 2

Product Used: LiOH Monohydrate (Process B)

466.04 g/mol 471.97 g/mol

At 25° C., 770.73 g (0.400 mol) of a 24.2% strength solution of the cyclohexenone oxime ether (II) in toluene are initially charged with stirring and diluted with 161.84 g of toluene, thus adjusting the concentration of the cyclohexenone oxime ether (II) to 20%. 200.99 g (0.420 mol) of a 8.8% strength LiOH monohydrate solution in MeOH (Chemetall; corresponds to a 5% strength solution based on LiOH (100%)) are then introduced over a period of 30 min. The mixture is stirred at 25° C. for 1 h. 381.21 g of a MeOH/toluene/water mixture are then distilled off at 50° C. under reduced pressure. During the distillation, the temperature is kept at 50° C. and the pressure is reduced in a controlled fashion from 450 mbar to 200 mbar. The distillation time is 230 min. Once the distillation has ended, a dash of methanol is added and the suspension is discharged from the stirred vessel onto a pressure nutsche. When the filtration has ended, the stirred vessel is rinsed with 174.00 g (200 ml) of fresh toluene and the filter cake is washed with this toluene. The filter cake is then washed twice with in each case 87.0 g (100 ml) of fresh toluene. The filter cake is then dried at 50° C. in a vacuum drying cabinet for 24 h. This gives 189.60 g of filter cake with a content of 96.5%. Taking this content into account, the yield is 97.0%.

Filtration Properties and Yields

Example 3

Determination of the Filter Resistances and the Filtration Times

The suspension of the lithium salt in toluene obtained after the distillation is charged to a 2.2 l pressure filter made of Hastelloy C 4 having a filter surface of 20 cm² and a filter cloth made of polypropylene (PP 2703). The pressure filter is then closed and a filtration pressure of 1 bar is applied. During the filtration, the pressure is kept constant and the time to gas breakthrough is measured. Finally, the filter is vented and opened and the thickness of the cake is measured.

Table 1 shows, in a comparative manner, filter resistances, filtration times and yields for the cyclohexenone oxime ether lithium salts (I) prepared by the processes mentioned.

The filter resistance $\alpha^*\eta$ stated in Table 1 is calculated using the formula:

$$\alpha^*\eta = 2^* t_F^* \text{filter surface}^* \text{filtration pressure}^* \text{volume of the filtrate}^{-1}{}^* \text{thickness of the filter cake}^{-1}$$

have little if any solvent power with respect to the active compound salts. The active compound concentration is about 10–30%, generally 20%.

Grinding is carried out in a Dyno-mill from Bachofen using a batch size of from 0.5 to 1 liter in a passage operation. In general after 5 passages (the slurry being pumped through the mill with the aid of a roller pump) mean particle sizes of 1–3 μm are achieved, according to microscopic evaluation.

Incorporation and dilution with further auxiliaries according to the recipes given below is then carried out by homogenizing for 10 minutes using a ground-glass or magnetic stirrer.

Practice of the Experiments

90% of the solvent (esters and/or aromatic solvents) and the auxiliaries stated (emulsifiers and dispersants) are initially charged according to the recipe given below, which is in each case identical, and the active compound (I) is added as a solid powder.

The formulation batch is then made up to 1 l (typical batch size) using the remaining solvent.

The batch is then ground as described above in a Dyno-mill using passage operation until about 60% of the particles

TABLE 1

Filter resistances and filtration times

| Process | Experiment | Filter resistances $\alpha^*\eta$ (mPas/M²) | Filtration time $t_F(s)$ | Yield (%) |
|---|---|---|---|---|
| Comparative Process A cyclohexenone oxime ether (II) + LiOH/H₂O (see Preparation Example 6 of WO 97/20807) | 1. Experiment | $2.2 \times 10^{13}$ | 7274 | 95.9% |
| | 2. Experiment | $5.6 \times 10^{13}$ | 18315 | 94.9% |
| | 3. Experiment | $2.0 \times 10^{14}$ | 65410 | 94.2% |
| Comparative Process B cyclohexenone oxime ether Na salt + LiCl (see Preparation Example 9 of WO 97/20807) | 1. Experiment | $3.8 \times 10^{11}$ | 138 | 89.8 |
| | 2. Experiment | $4.1 \times 10^{11}$ | 151 | 90.2 |
| Process A according to the invention cyclohexenone oxime ether (II) + LiOH (98%) in MeOH (see Preparation Example 1). | 1. Experiment | $3.2 \times 10^{11}$ | 103 | 94.1 |
| | 2. Experiment | $3.9 \times 10^{11}$ | 115 | 94.5 |
| | 3. Experiment | $3.6 \times 10^{11}$ | 102 | 93.8 |
| Process B according to the invention cyclohexenone oxime ether (II) + LiOH monohydrate (57%) in MeOH (see Preparation Example 2) | 1. Experiment | $3.5 \times 10^{11}$ | 107 | 97.0 |
| | 2. Experiment | $2.1 \times 10^{11}$ | 56 | 96.7 |
| | 3. Experiment | $3.7 \times 10^{11}$ | 130 | 95.9 |

The best filtration properties and yields are obtained when the cyclohexenone oxime ether Li salts (I) are prepared by the processes according to the invention according to Example 1 and 2.

Oil SC Formulations

Example 4

General Experimental Description of the Preparation of Oil SC Formulations

Using glass beads (diameter: 0.9–1.2 mm) as an aid for grinding, the lithium salts (I) are ground at about 0° C. with the lipophilic solvents—here generally liquid media which have a size of less than 2 μm (microscopic evaluation). Typically, this requires 5 passages.

| Recipe: | 75 g/l | of (I) |
|---|---|---|
| | 250 g/l | of Aerosol OT-A |
| | 50 g/l | of Emulpon EL 20 |
| | 500 g/l | of methyl oleate |
| | ad 1 l | Solvesso 150 |

Table 2 shows stability data of the cyclohexenone oxime ether Li salts (I) prepared by the individual processes.

TABLE 2

| Process | Oil SC storage stability in % (rel.) after 14–28 d at 54° C. | |
|---|---|---|
| | 2 Weeks 54° C. | 4 Weeks 54° C. |
| Comparative Process A cyclohexenone oxime ether (II) + LiOH/H₂O (see Preparation Example 6 of WO 97/20807) | 93.4 | 88.2 |
| Comparative Process B cyclohexenone oxime ether Na salt + LiCl (see Preparation Example 9 of WO 97/20807) | 94.2 | 91.2 |
| Process A according to the invention cyclohexenone oxime ether (II) + LiOH (98%) in MeOH | 95.6 | 94.8 |

It is found that, after a storage time of 4 weeks at 54° C., the lithium salt prepared by process A according to the invention, for example, has considerably better storage stability than a comparable lithium salt prepared according to the prior art.

The invention claimed is:

1. A process for preparing 2-{1-[2-(4-chlorophenoxy)propoxyimino]butyl}-3-hydroxy-5-(tetrahydrothiopyran-3-yl)cyclohex-2-enone lithium salt of the formula (I),

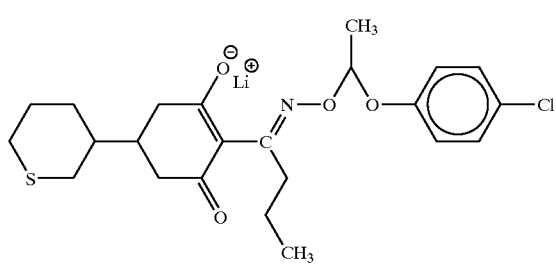

(I)

by reacting 2-{1-[2-(4-chlorophenoxy)propoxyimino]butyl}-3-hydroxy-5-(tetrahydrothiopyran-3-yl)cyclohex-2-enone of the formula (II)

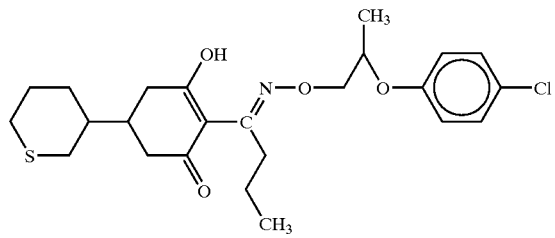

(II)

and lithium hydroxide in a solvent mixture and isolating the compound of the formula (I), wherein the solvent mixture comprises at least one aromatic hydrocarbon and methanol and at least some of the solvent is removed prior to the isolation.

2. A process as claimed in claim 1, wherein the aromatic hydrocarbon used is toluene.

3. A process as claimed in claim 1, wherein the solution of the compound of the formula (II) comprises the compound in a concentration of from 5 to 40% by weight.

4. A process as claimed in claim 1, wherein the lithium hydroxide solution comprises LiOH in a concentration of from 1 to 7% by weight.

5. A process as claimed in claim 1, wherein the reaction is carried out at a temperature of from −2° C. to 60° C.

6. A process as claimed in claim 1, wherein the solvent is removed by distillation.

7. A process as claimed in claim 6, wherein the distillation is carried out at temperatures of from 20° C. to 70° C.

8. A process as claimed in claim 6, wherein the distillation is carried out at a substantially constant temperature.

9. A process as claimed in claim 6, wherein such an amount of solvent is removed that the compound of the formula (I) precipitates out substantially completely.

10. A process as claimed in claim 1, wherein the isolation is carried out by filtration or centrifugation.

11. A process as claimed in claim 3, wherein the concentration of the compound of the formula (II) is from 10 to 30% by weight.

12. A process as claimed in claim 3, wherein the concentration of the compound of the formula (II) is about 20% by weight.

13. A process as claimed in claim 4, wherein the lithium hydroxide concentration is from 2 to 6% by weight.

14. A process as claimed in claim 4, wherein the lithium hydroxide concentration is about 5% by weight.

15. A process as claimed in claim 5, wherein the reaction temperature is from 0° C. to 40° C.

16. A process as claimed in claim 5, wherein the reaction temperature is from 20° C. to 30° C.

17. A process as claimed in claim 7, wherein the distillation temperature is from 30° C. to 60° C.

18. A process as claimed in claim 7, wherein the distillation temperature is from 40° C. to 50° C.

* * * * *

UNITED STATES PATENT AND TRADEMARK OFFICE
CERTIFICATE OF CORRECTION

PATENT NO.        : 6,989,453 B2
APPLICATION NO.   : 10/380107
DATED             : January 24, 2006
INVENTOR(S)       : Maywald et al.

Page 1 of 1

It is certified that error appears in the above-identified patent and that said Letters Patent is hereby corrected as shown below:

Claim 5: Column 16, lines 26 – 27, "-2°C to 60°C" should read -- -20°C to 60°C--

Signed and Sealed this

Third Day of April, 2007

JON W. DUDAS
*Director of the United States Patent and Trademark Office*